United States Patent [19]

Rincoe

[11] Patent Number: 5,728,175
[45] Date of Patent: Mar. 17, 1998

[54] ARTIFICIAL ANKLE JOINT WITH CUSHION STRUCTURES AND PROSTHETIC DEVICES FORMED THEREWITH

[76] Inventor: Richard G. Rincoe, 49 S. Holman Way, Golden, Colo. 80401

[21] Appl. No.: 538,750

[22] Filed: Oct. 3, 1995

[51] Int. Cl.$^6$ ........................................... A61F 2/66
[52] U.S. Cl. ................................. 623/49; 623/52
[58] Field of Search ........................ 623/52, 50, 47, 623/49, 38, 35, 53, 55, 48, 51, 54, 56

[56] References Cited

U.S. PATENT DOCUMENTS

| | | | |
|---|---|---|---|
| 1,069,409 | 8/1913 | Gainos et al. | 623/52 |
| 1,071,230 | 8/1913 | Hanger | 623/50 |
| 1,112,819 | 10/1914 | McFarland | 623/49 |
| 2,475,372 | 7/1949 | Catranis | 623/49 |
| 2,617,115 | 11/1952 | Ellery | 623/52 |
| 2,843,853 | 7/1958 | Mauch | 623/52 |
| 5,425,780 | 6/1995 | Flatt et al. | 623/38 |

FOREIGN PATENT DOCUMENTS

| | | | |
|---|---|---|---|
| 0180745 | 12/1917 | Canada | 623/52 |
| 2653327 | 4/1991 | France | 623/52 |
| 0299321 | 7/1917 | Germany | 623/53 |
| 1211354 | 2/1966 | Germany | 623/49 |
| 2216423 | 10/1989 | United Kingdom . | |
| 9100070 | 1/1991 | WIPO | 623/53 |

*Primary Examiner*—David H. Willse
*Attorney, Agent, or Firm*—Timothy J. Martin

[57] ABSTRACT

An ankle joint, and a prosthetic device incorporating such ankle joint, pivots to imitate the action of a normal ankle and foot. The ankle joint includes a socket secured to an artificial foot and a shank portion that connects at a distal end of a residual lower leg extremity. The shank has a head that is rotatably mounted in the socket so that it pivots between first and second positions about a neutral position. Springs bias the shank into the first position corresponding to plantar-flexion orientation of the foot. A first cushion attenuates pivoting action and force of impact at the first position, and an optional second cushion attenuates pivoting action and force of impact at the second position. The socket is connected to the foot by a mounting plate assembly, and side bumpers are provided to resist lateral torque forces. The pitch of the socket, and thus the shank portion, is selectively adjustable. A locking mechanism acts to releasably lock the ankle joint in the neutral position when under a compressive load from the weight of the amputee. The ankle is constructed with elements that reduce mechanical noise during use.

18 Claims, 7 Drawing Sheets

ARTIFICIAL ANKLE JOINT WITH CUSHION STRUCTURES AND PROSTHETIC DEVICES FORMED THEREWITH

FIELD OF INVENTION

The present invention relates to prosthetic devices adapted for use on the lower extremities of amputees. More particularly, the present invention is directed to an artificial ankle, and a prosthetic leg device incorporating such ankle, that pivots to provide an amputee with ambulatory support during a variety of activities. This invention specifically concerns artificial ankles which permit and mimic typical movement capabilities of a non-amputee.

BACKGROUND OF THE INVENTION

As described in my co-pending application, Ser. No. 08/315,985 entitled ARTIFICIAL ANKLE AND PROSTHETIC DEVICES FORMED THEREWITH, appropriate medical care has sometimes required amputation of a diseased or damaged limb. When the leg or portion thereof is amputated, the leg amputee is often fitted with a prosthetic leg device enabling the amputee to walk without the use of crutches or other support devices. An early prosthetic leg device was simply a peg affixed to the remaining portion of the amputated leg of the amputee. Although somewhat effective, a "pegged" leg was not aesthetically pleasing.

Technological advancements, including advancements in materials technology, have enabled other types of prosthetic leg devices to be developed. Typically, these prosthetic leg devices have included a calf portion, an ankle and a foot structure that is similar to the human leg in order to be more aesthetically pleasing. Fabrication of these prosthetic leg devices have made them simulate a real leg and real foot structure unless closely scrutinized. Materials utilized for use of such prosthetic leg devices included plastic or rubber like material having a color and texture of human flesh. With fabrication, footwear could be worn on the artificial foot to match footwear on the healthy leg and foot so that the general public, without close scrutiny, would be unable to visually determine that the person was an amputee.

Even though these new prosthetic devices were generally lifelike in appearance, several disadvantages remained in use and in the mechanical action during ambulatory activities. First, in order to assure proper balance, the lower leg portion below the "knee" was typically rearwardly offset from the upper leg portion above the "knee". Therefore, in simply standing, the artificial foot on the prosthetic device became positioned laterally and rearwardly of the real foot, in a staggered orientation, which presented an unnatural appearance. More importantly, though, none of the devices performed functionally as well as a human leg.

As is well known, a normal cycle of a human includes three general phases which are dorsiflexion, plantarflexion and "push-off". Each of these phases may be explained relative to an angular position of the foot relative to the shin bone. The foot, of course, includes a heel disposed proximately to the ankle joint and a sole disposed distally of the ankle joint. The human foot is considered to be in a neutral position when it forms a 90° angle with the shin bone relative to the pivotal axis of the ankle joint. Dorsiflexion occurs when an acute angle is formed between the foot and the shin bone relative to the pivotal axis of the ankle joint, and this position is also known simply as "flexion". On the other hand, plantarflexion occurs when an obtuse angle is formed between the foot and the shin bone relative the pivotal axle of the ankle. Plantarflexion is also sometimes referred to as "extension". "Push-off" occurs as the trailing leg completes its step with the ankle joint locked relative to the foot and shin bone in the neutral position so that the muscles in the foot can propel the body weight of the walking person forward to transfer the person's weight onto the advanced leg.

Unlike the function of a healthy human ankle, the typical ankle of the prosthetic leg device has usually been constructed as a rigid joint establishing a 90° connection with the foot in the neutral position. By such rigid connection, no pivotal motion was provided between the foot and the leg portion of the prosthetic device. The reason for providing such rigid connection was to allow the amputee to "push-off" during his/her gait cycle. Due to the inability of such devices to undergo dorsiflexion and plantarflexion, however, the amputee was required to angularly and swing his/her prosthesis in an arcuate motion laterally relative to his/her healthy leg when making a stride. Otherwise, the toe of the prosthetic device would catch or become "stubbed" on the walking surface or dragged when stepping. The arcuate motion has been noted to add to stress to the healthy knee, leg and ankle of the amputee that can result in chronic pain and further injury. The lack of dorsiflexion and plantarflexion further hindered the amputee when ascending or descending stairs or while engaged in other ambulatory and similar activities wherein foot motion is important. Such events include sporting events which require running, horseback riding and the like.

Some developments have been made to provide a prosthesis with an artificial ankle that can pivot about the normal ankle pivot axis. In U.S. Pat. No. 2,843,853 issued Jul. 22, 1958 to Mauch, one such a pivoting ankle is shown. In this patent, the foot is normally biased in the neutral position and front and rear springs were provided to maintain this position. In my co-pending patent application, improvements were described with respect to pivoting ankles to provide, among other features, a locking mechanism to lock the foot in the neutral position when under a load but to release the foot from the neutral position and to bias the foot into the dorsiflexion position so that the residual limb and the prosthetic device may be advanced during the amputee's gait in a normal manner.

Despite the advances made in the past, there remains a need for improved pivoting ankle joints which may be incorporated in the prosthetic devices for leg amputees in order to more closely imitate the functioning of the normal human ankle. A further need was for such pivoting ankle joints of simplified construction which would enable an amputee to engage in a variety of ambulatory and sports activities in a more natural manner. A further need exists for pivoting ankle joints, and prosthetic devices formed therewith, which are versatile in use and which parts may be readily replaced at a reduced costs.

SUMMARY OF INVENTION

It is an object of the present invention to provide a new and useful ankle joint for prosthetic devices which closely imitates the motion of a natural human foot.

Another object of the present invention is to provide a pivoting ankle joint for use with a prosthetic devices as an improvement therefor which ankle joint is simplified in construction.

Yet another object of the present invention is to provide a pivoting ankle joint for use with prosthetic devices which is durable yet which is constructed so that worn parts may be easily replaced.

Still a further object of the present invention is to provide a pivoting ankle joint that provides cushions at one or both extrema of pivotal motion so as to attenuate impact forces at these extrema.

It is still a further object of the present invention to provide a pivoting ankle joint constructed so as to allow a user to tailor the performance of the ankle joint for different physical situations.

A further object of the present invention is to provide a pivoting ankle joint that resiliently resists lateral deflections or torque forces about the longitudinal axis of the foot.

It is yet another object of the present invention to provide a pivoting ankle joint that is adjustable in pitch.

Another object of the present invention is to provide a pivoting ankle joint that includes a locking mechanism to allow push-off, but which also includes a lock disable structure to disable the locking mechanism.

To accomplish these objects, the present invention is directed to a pivoting ankle, in a prosthetic device incorporating such ankle which provides improved structure for use by an amputee. In its broad form, the prosthetic device includes a proximal portion adapted to be secured to a residual leg extremity of the amputee. A distal foot structure then extends along a longitudinal axis, and a mounting base assembly is secured to the foot structure. A matable socket and head assembly interconnects the proximal portion of the prosthetic device and the distal foot structure. This socket and head assembly includes a socket disposed on one of the proximal end structure and the foot structure and a head sized to matably received by the socket and disposed on the other of the proximal end portion and the foot structure. Preferably, the socket structure is mounted to the mounting base assembly and has a cavity formed therein which is sized and adapted to receive a head element for rotational movement therein. This head is part of a shank portion that includes a shaft adapted to mount to the proximal portion of the prosthetic device. The shank portion thus defines a leg axis and is pivotal about a pivot axis with respect to the socket structure. Thus, the foot portion may move between a first position corresponding to plantarflexion and a second position corresponding to dorsiflexion about a central or neutral position of a human foot. A cushion element is then associated with the ankle joint and is operative to attenuate impact forces resulting from relative pivotal movement of the head and shank at the first pivot position. Preferably, a second cushion element is provided to attenuate relative pivotal movement at the second pivot position.

In the exemplary embodiment of the invention, the socket is secured to the mounting plate assembly by means of a swivel connector, and adjustment bolts are provided so as to allow selected adjustment of the pitch of the leg axis relative to the longitudinal axis of the foot. The use of these adjustment bolts allow the angle between the bottom of the socket to be varied with respect to the plane of the mounting plate. Preferably, torsional springs are provided to bias the ankle joint into the first or plantarflexion position, and these torsional springs are mounted in cavities formed in the head that is received in the socket. One end portion of the torsional springs are then mounted relative to the socket while the other end portions are mounted to the head to accomplish this biasing. Moreover, it is preferred that a load-sensitive locking mechanism be associated with this socket and head assembly with this locking mechanism being operative in response to a triggering compressive force in excess of a threshold magnitude to cause the head to lock relative to the socket at a selected locking position corresponding to the neutral position. A lock disable mechanism is provided, in the form of an L-shaped lever arm, that is selectively operable to disable the load-sensitive locking mechanism so that the load-sensitive locking mechanism is prevented from locking the head and the socket at the selected locking position even in the presence of the triggering compressive force.

The first and second cushions are preferably received in cushion cavities respectively located at the rearward and forward upper edges of the socket. Here, a shoulder plate is bounded on the shaft of the shank portion that is connected to the rotatable head. This shoulder plate is oriented so that it has a pair of flat faces which contact the first and second cushions at the extreme limits of the pivotal motion thereby to cushion the rotation of the shank portion, and correspondingly, the head, at the extrema.

In order to compensate for torsional forces about the longitudinal axis of the foot, a pair of resilient bumpers are provided. Preferably, these bumpers are interposed between the socket and the mounting plate so that, as the socket attempts to pivot laterally from side-to-side, these bumpers resist the lateral torsional forces. The combined effect of the bumpers along with the pitch adjustment elements and the pivoting, load-locking ankle closely imitates, then, the natural action of a human foot.

These and other objects of the present invention will become more readily appreciated and understood from a consideration of the following detailed description of the exemplary embodiment of the present invention when taken together with the accompanying drawings, in which:

DETAILED DESCRIPTION OF THE EXEMPLARY EMBODIMENTS

The present invention broadly concerns ankle joints for use in prosthetic devices and prosthetic devices incorporating the same. The ankle joint according to the exemplary embodiment of the present invention is constructed so as to minimize component parts and the cost of assembly while at the same time providing an ankle joint which closely imitates the normal human ankle. Specifically, the ankle according to the present invention articulates between a first (plantarflexion) position and a second (dorsiflexion) position about a third (neutral) position so as to allow a normal human gait. The present invention incorporates structure to reduce the impact between the residual limb and the prosthetic device during use as well as to allow better balance when employed. Moreover, the improved ankle of the present invention allows the amputee to engage in a variety of activities, including sports activities. This invention also provides for various adjustment features. As such, the ankle according to the present invention is an improvement over the ankle joint shown in my earlier U.S. application Ser. No. 08/315,985.

Figures 1, 2:
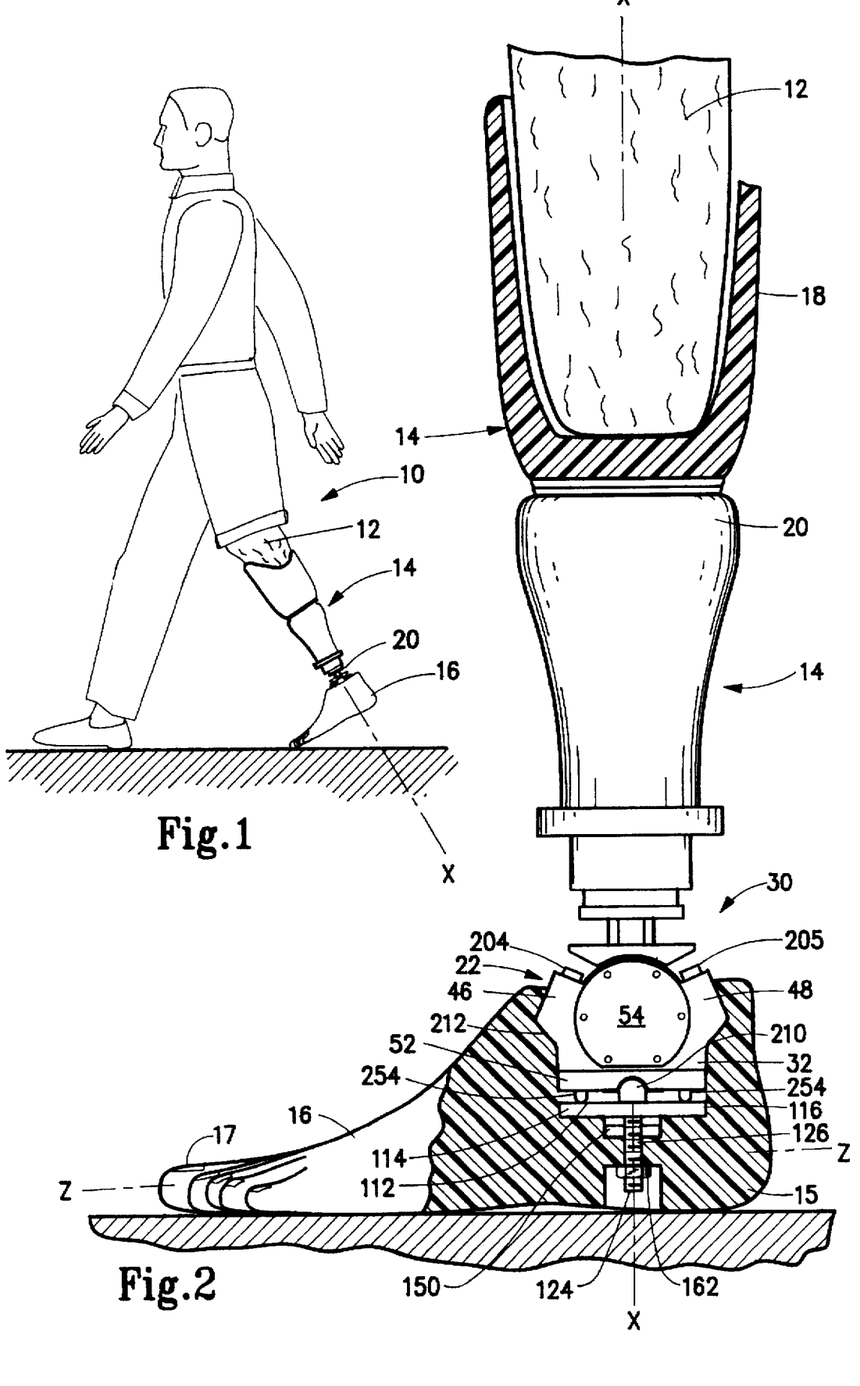
FIG. 1 is a side view in elevation illustrating an amputee walking with a prosthetic in the "push-off" position.
FIG. 2 is a side view in elevation and a partial cross-section showing the residual limb in a prosthetic device incorporating the pivoting ankle according to the exemplary embodiment of the present invention.

As is shown in FIG. 1, then, amputee 10 has a residual limb 12 onto which prosthetic device 14 is mounted. Amputee 10 is shown in mid-stride wherein prosthetic device 14 has a foot portion 16 oriented in a "neutral" position for "push-off" during such stride. Prosthetic device 14 includes an ankle joint 20 according to the exemplary embodiment of the present invention.

As is shown in greater detail in FIG. 2, prosthetic device 14 has a proximal portion including a socket 18 sized and adapted to receive the distal end portion of residual limb 12 and a shin portion 20 which simulates the lower leg and calf of a human leg. Foot portion 16 is formed at a distal end of prosthetic device 14 and is interconnected to shin portion 20 by means of artificial ankle joint 30. Foot portion 16 is molded out of stiff plastic or rubber-like material, as is known in the art, but includes a cavity 22 that is operative to receive ankle joint 30. Foot portion 16 extends along a longitudinal axis "Z" as shown in this figure.

Figures 3, 4, 5:
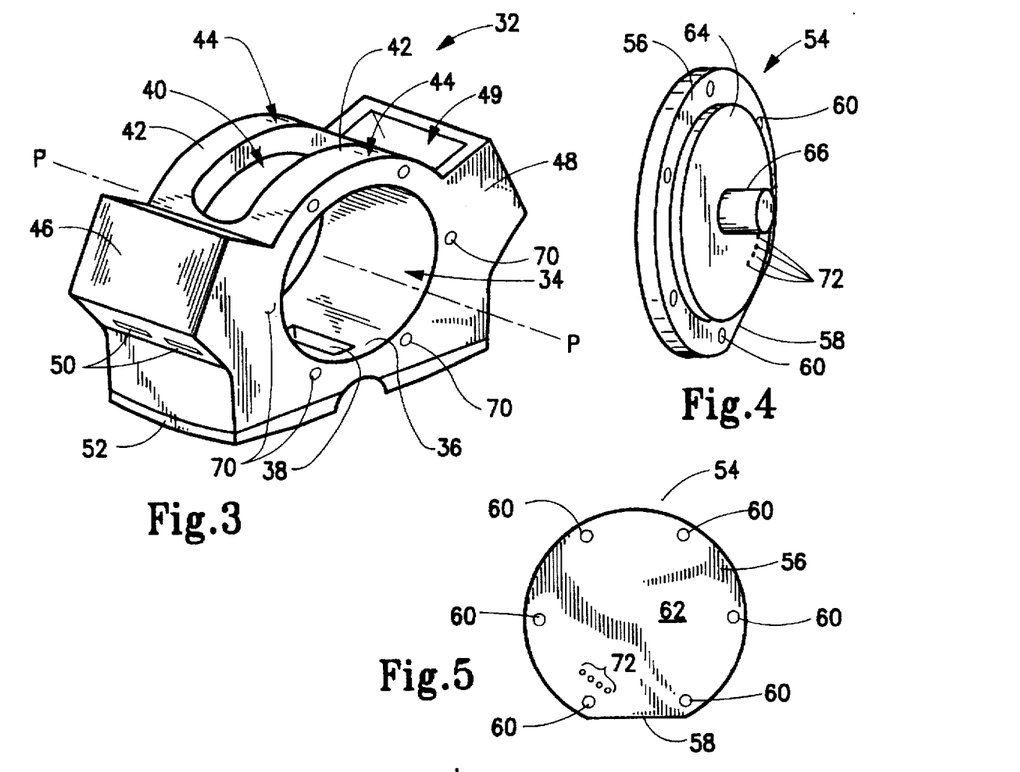
FIG. 3 is a prospective view of the socket housing structure used with the pivoting ankle in the exemplary embodiment of the present invention.
FIG. 4 is a perspective view showing the inside surface area of a side closure used with the socket housing structure of FIG. 3.
FIG. 5 is a side view in elevation showing the outer surface of the side closure of FIG. 4.

The structure of ankle joint 30 is best shown in FIGS. 3–7, 10(a)–10(c) and 11. In these figures, it may be seen that ankle joint 30 includes a housing or socket structure 32 preferably formed of a high impact plastic material or metal, such as aluminum. Socket structure 32 includes a cylindrical cavity 34 extending transversely therethrough so as to have an arcuate sidewall 36. A channel 38 extends through arcuate sidewall 36 at a lowermost portion thereof and a diametrically ovoid opening 40 is located opposite channel 38. Accordingly, as is shown in FIG. 3, socket structure 32 includes a pair of upper arcuate bands 42 having an outer surfaces 44 formed along the surface of an imaginary cylinder that is concentric with cylindrical cavity 34. A pair of cushion chambers, including front cushion chamber 46 and rear cushion chamber 48 are formed integrally with socket structure 32 and respectively form cushion cavities 47 and 49, respectively. Each of chambers 46, 48 include passageways, such as passageways 50 shown with respect to front cushion chamber 46, and each of these passageways 50 communicates with the interior of the respective cushion cavity in order to allow fluids to drain therefrom should the prothesis be worn in a wet environment. A plate 52 is located at a bottom of socket structure 32.

Figure 6:
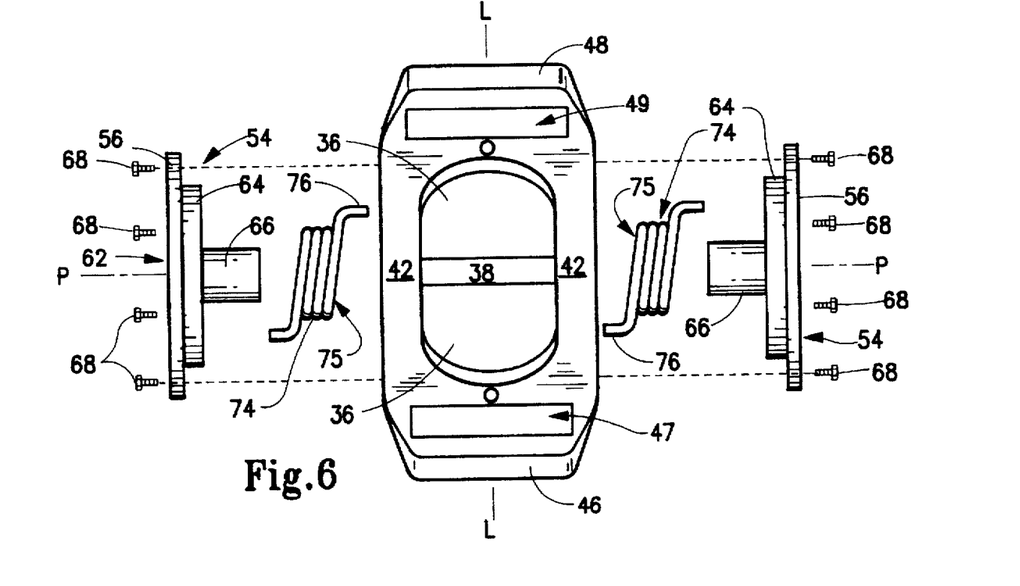
FIG. 6 is an exploded top plan view of the socket housing of FIG. 3 also showing the torsional springs for biasing the ankle into the second or dorsiflexion position.

A pair of disc-shaped side closures 54 are provided to enclose cavity 34. Disc-shaped side closures 54 are best shown in FIGS. 4–6. In these Figures, it may be seen that side closures 54 include an outer circular plate 56 that has a flattened edge 58 and through which a plurality of openings 60 is formed around the periphery thereof. Each of closures 54 has a flat outer surface 62 and an opposite inner surface upon which is disposed a raised circular plateau 64 which has a diameter that is the same as cavity 34 so that it may seat therein. A central post 66 extends axially of plateau 64 so that, when each of side closures 54 are mounted on socket structure 32, as is shown in FIG. 6, posts 66 are oriented coaxially with pivot axis "P". As is shown also in this Figure, a plurality of screws 68 may extend through holes 60 and be threadably received in threaded bores 70 (FIG. 3). Moreover, as is shown in FIGS. 4 and 5, a plurality of bores 72 extend through circular plate 56 and plateau 64 in order to provide for adjustable mounting of torsional springs 74, shown in FIG. 6.

Figure 10A:
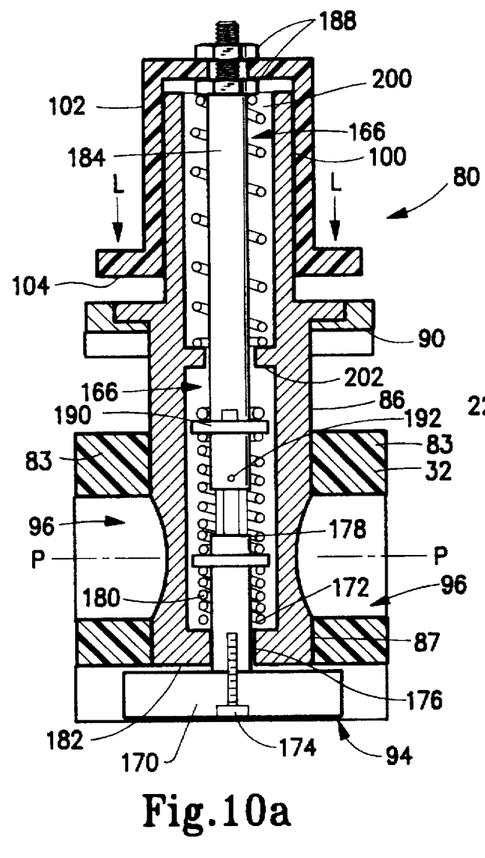
FIGS. 10(a)–10(c) are side views in cross-section showing the locking mechanism of the exemplary embodiment of the present invention in a loaded state (dorsiflexion) for locking in the neutral position and in an unloaded state, respectively.
Figure 10B:
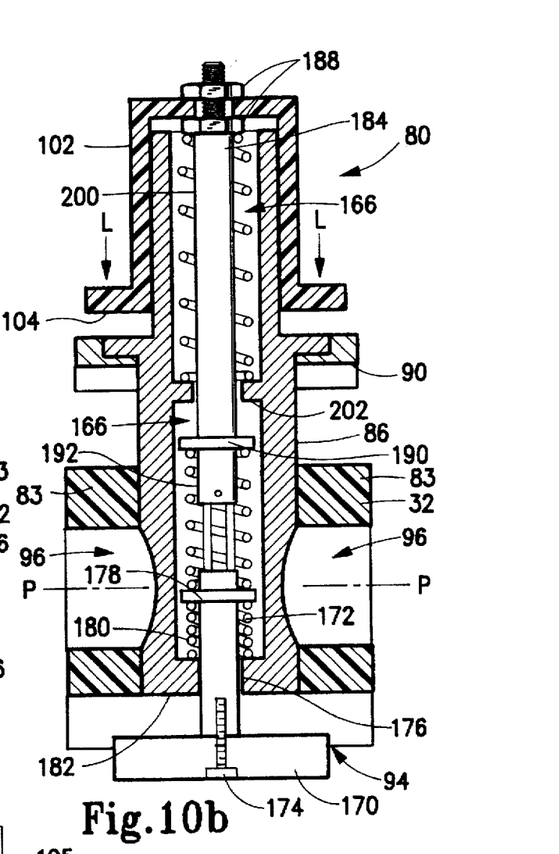
Figure 10C:
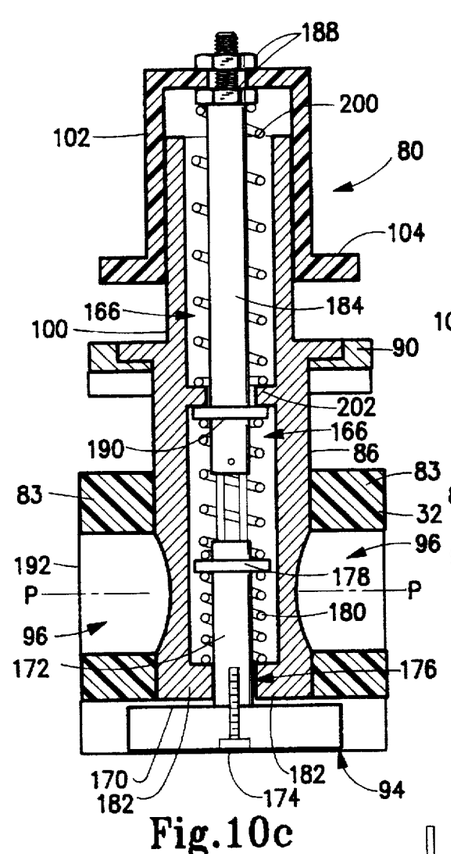

With reference to FIGS. 7 and 10(a)–10(c), it may be seen that ankle joint 30 includes a shank portion 80 that has a distal head 82 that is generally cylindrical in the transverse direction and which is sized and adapted for close-fitted, mated engagement in cavity 34. Here again, the material used to construct shank portion 80 may be plastic or metal. Head 82 has a central axis that is oriented coaxially with pivot axis "P" when in the mounted state in cavity 34. Accordingly, head 82 has a cylindrical outer surface 84 that is in sliding contact with arcuate sidewall 36 of cavity 34. A cylindrical shaft 86 extends radially outwardly from head 82 and terminates in an outer shoulder 88 to which is secured a plate 90 by means of screws 92, shown in phantom in FIG. 7. As is shown in FIGS. 10(a)–10(c), head 82 may be constructed in several pieces so that it may be assembled internally of cavity 34 since head 82 is larger in size than ovoid opening 36. Here, it may be seen that head 82 is formed by a pair of side pieces 83 that are generally cylindrical and that are mounted to shaft 86 that is flattened at an end 87. Side pieces 83 are fastened to one another by bolts 85 which extend through bores formed in each of side pieces 83 and through flattened end 87 of shaft 86.

Figure 7:
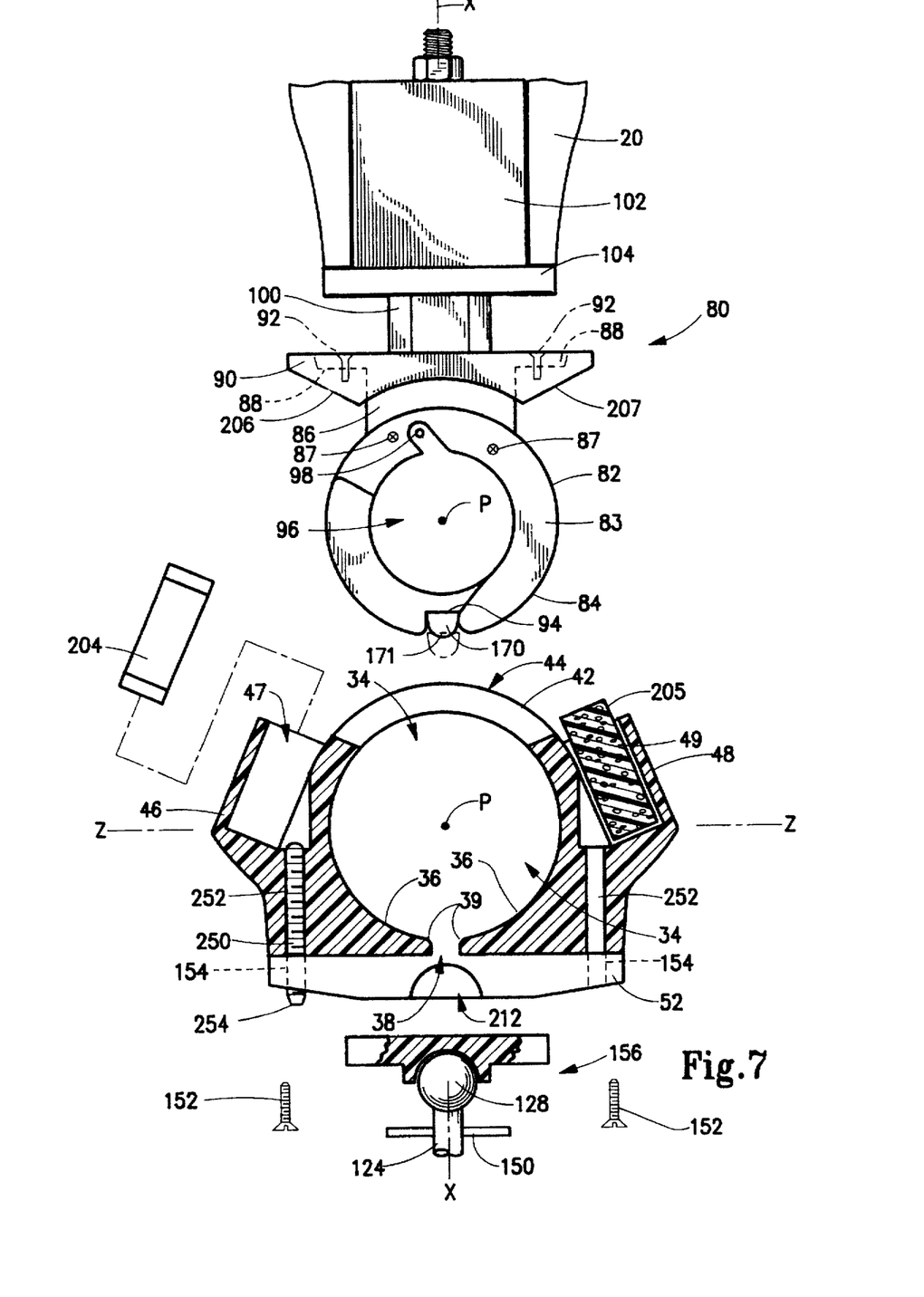
FIG. 7 is a side view in partial cross-section and exploded to show the structure of the pivoting ankle according to the exemplary embodiment of the present invention.

A channel 94 is oriented diametrically opposite shaft 86 and extends longitudinally head 82 parallel to the central axis thereof. Channel 94 is sized and adapted to receive locking bar 170, the function and structure of which is described more thoroughly below. Furthermore, as is shown in FIGS. 7 and 10(a)–10(c), side pieces 83 of head 82 each includes a cylindrical spring cavities 96 which are aligned coaxially and that are sized and adapted to receive torsional springs 74 and posts 66 of side closures 54. With reference, then, to FIG. 6 and 7, it may be appreciated that a torsional spring 74 may be received in cavity 96 with a prong 76 thereof received in bore 98. Side closures 54 may then be mounted onto socket structures 32 with posts 66 being inserted into the interior 75 of spring 74 with a prong 78 opposite prong 76 being received in a selected one of bore 72 inside closures 54. By selecting different bores 72 for receipt of prong 76, each of springs 74 may be pre-loaded to increase or decrease the biasing force thereof, as described more thoroughly below.

Shank portion 80 is mountable to shin portion 20 of prosthetic device 14. To this end, a hexagonal shaft 100 extends radially from head portion 82 and is formed integrally and coaxially with shaft 86. A cap 102 is slidably and telescopically received on hexagonal shaft 100, with cap 102 having a distal rim 104 which provides a seat against which shin portion 20 may rest. Shin portion 20 may be secured onto cap 102 in any convenient manner, as is known in the art. Moreover, as is described more thoroughly below, cap 102 is retained on shank portion 80 by means of rod 184 of the locking mechanism. By configuring shaft 100 in a hexagonal shape, cap 102 is keyed against rotation about leg axis "X".

Figure 8:
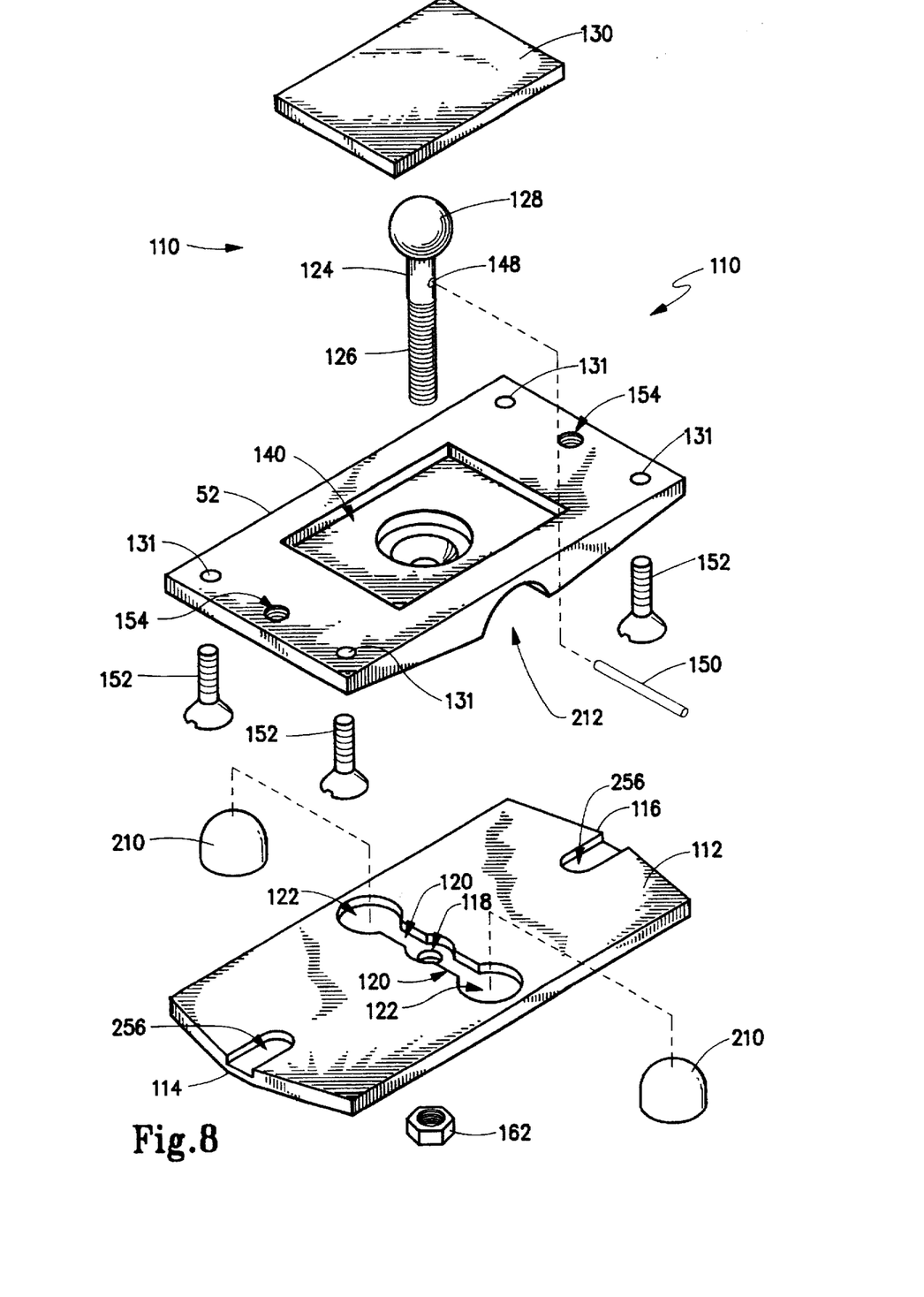
FIG. 8 is an exploded perspective view showing the base plate assembly of the pivoting ankle according to the exemplary embodiment of the present invention.

With reference to FIGS. 2 and 7–9, it may now be readily appreciated that socket structure 32 and, correspondingly, shank portion 80 may be mounted with respect to foot portion 16 for relative pivotal motion between first (plantarflexion) and second (dorsiflexion) positions. To accomplish this, a base plate assembly 110 is provided. As is best shown in FIG. 8, base plate assembly 110 includes a generally rectangularly shaped flat base plate 112 that has a front end 114 and a rear end 116. Base plate 112 includes a central circular opening 118 which is intersected by a transverse channel 120 that terminates in opposite circular recesses 122. A threaded bolt 124 has a threaded shaft 126 which extends through opening 118 and terminates in an enlarged spherical ball 128 opposite threaded shaft 126. Ball 128 is captured by a socket connector formed by a pair of mounting plate 130 and plate 52 of socket 32, best shown in FIGS. 7 and 9. As is shown in these Figures, mounting plate 130 is rectangular in shape and includes a post 132 formed along a central axis thereof. Post 132 includes a hemispherical cavity 134 sized to receive half of the volume of ball 128. Correspondingly, plate 52 is formed as a rectangular plate having an enlarged post 138 formed along a central axis thereof. A rectangular cavity 140 is formed in mounting plate 136 with cavity 140 being sized to nestably receive mounting plate 130. Cavity 140 has a cylindrical portion 142 that is correspondingly sized to receive post 132 of mounting plate 130 and a hemispherical cavity portion 144 which is sized to receive half of the volume of ball 128. A bore 146 communicates with hemispherical cavity 144 and is sized to receive shaft 126 of bolt 124.

Figures 9, 11:
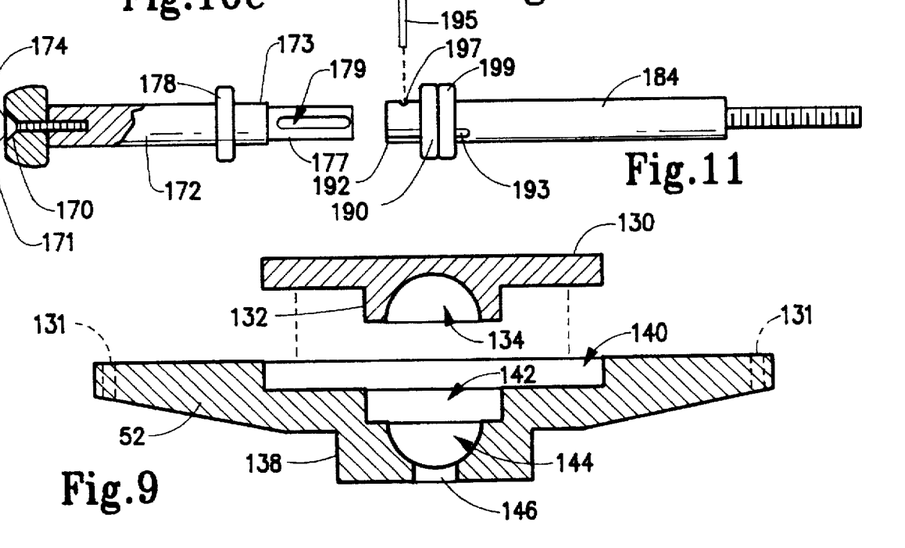
FIG. 9 is an exploded view showing the mounting plates used to connect the artificial ankle of the present invention to a prosthetic foot.
FIG. 11 is an exploded side view in elevation of the rods forming part of the locking mechanism of the present invention.

To assemble this ball and socket connection, then, shaft 126 of bolt 124 is inserted through cavity 140 and, specifically, through bore 146. Bolt 124 is then pinned into position by means of a press-fit pin 150 which extends through diametric passageway 148 formed in bolt 126 proximate to ball 128. One half of ball 128 is therefore received in hemispherical cavity portion 144 in plate 52. Mounting plate 130 is then superimposed onto mounting plate 136 so that post 132 is inserted in and telescopically received in mated engagement by cylindrical cavity portion 142 so that plates 130 and 136 are in abutting relationship. The other half of ball 128 is therefore received in hemispherical cavity 134. Screws 152 then are mounted through holes 131 in plate 52 and are threadably engaged in corresponding threaded bores in socket structure 32 (not shown).

With reference to FIG. 2 and 8, it may be seen that bolt 124 is secured to mounting plate assembly 110 by means of pin 150. This assembled structure, including base plate assembly 110, socket 32 and shank portion 80 may then be inserted into recess 22 and foot portion 16 with threaded shaft 126 of bolt 124 extending through bore 160 to be secured by a second nut 162 with front end 114 of base plate 112 facing toes 17 of foot portion 16 with rear end 116 of base plate 112 facing heel 15 of foot portion 16. A relative canting of socket structure 32 with respective to base plate 112 may be accomplished by adjusting bolts 250, such as shown in FIGS. 2 and 7. Here, it may be seen that socket structure 32 is provided with a pair of bores 252 are aligned with threaded holes 154 in plate 52 secured thereto. Adjusting bolts 250 may extend through bores 252 so that heads 254 thereof may be received in slots 256 (FIG. 8) so that heads 254 bear against base plate 112. By tightening or loosening bolts, such as bolts 250, the angle between the bottom of socket structure 32 and base plate 112 may be adjusted. This adjustment permits the amputee to select an engagement angle for the locking mechanism, described below, that is other than vertical as is appropriate for his/her posture and walking stride. Moreover, the adjustment permits turning the ankle joint and prosthesis for shoes having different heel heights.

The locking mechanism of the present invention may be best seen in FIGS. 10(a)–10(c) and 11, and it should be understood that this locking mechanism operates substantially identically with the locking mechanism shown in my corresponding U.S. application Ser. No. 08/315,985. In FIGS. 10(a) 10(c), then, it may be seen that shafts 86 and 100 have a cylindrical axial passageways 166 formed therethrough. A locking bar 170, shown in FIGS. 7 and 10(a) –10(c) is matably receivable in channel 94 of distal head 82. A first rod 172 is fastened to locking bar 170 by means of screw 174. First rod 172 extends radially from a medial portion of locking bars 170 through a hole 176 in a distal end of shaft 86 to communicate with the interior thereof. An annular shoulder 178 is located at the interior end 173 of first rod 172 with the interior end 173 of rod 172 terminating in a flat eyelet 177 having a slot 179 formed therethrough. A first spring 180 is confined between shoulder 178 of rod 172 and shoulder 182 of shaft 86.

A second rod 184 has a first end 186 secured by a pair of nuts 188 to cap 102 so that cap 102 is mounted thereon. Annular shoulder 190 is located proximally to a distal end 192 of rod 184 that is located in the interior of passageway 166. End 192 has a slit 193 formed therein with slit 193 being sized and adapted to mate with eyelet 177 for relative axial movement toward and away from one another. A pin 195 is inserted through holes 197 and slot 179 after eyelet 177 is placed in slit 193 to prevent complete separation of rods 172 and 184. A rubber O-ring 199 is mounted on rod 184 adjacent to annular shoulder 190 but on an opposite side thereof from end 192. A second spring 192 is confined between shoulders 178 and 190, and it should be appreciated that second spring 192 has a smaller spring constant than first spring 180. A third spring 200 is positioned between cap 102 and interior shoulder 202 that is formed integrally with shafts 86 and 100 in passageway 166. Spring 200 has a substantially larger spring constant than either springs 180 and 192 and is selected to compressibly bear the weight of the amputee. Spring 200 compresses to allow cap 102 to descend downwardly toward plate 90 and, upon removal of the amputee's weight, generates a restoring force that acts to provide a push off the trailing prosthesis during the stride.

With reference specifically to FIG. 10(a), it may be seen that when no load is placed on cap 102, springs 180 and 192 both bias locking bar 170 into recess 94 and bias cap 102 away from plate 90 and thus socket structure 32. However, when a sufficient loading force "L" is placed on cap 102 such as by the weight of the amputee, this load overcomes the resilient force provided by spring 200 and also springs 178, 192. Accordingly, cap 102 is telescoped to the position proximately to plate 90 and socket structure 32. Correspondingly, unless restrained, this load causes locking bar 170 to move out of recess 94. Should movement of locking bar 170 be restricted, however, as is shown in FIG. 10(c), this loading force "L" acts to compress spring 192.

In order to minimize audible noise during the engagement and disengagement of locking bar 190, it may be appreciated in reference to FIG. 7 that channel 38 is formed by rounded sidewalls 39. Likewise, the distal surface 171 of locking bar 170 is rounded thereby providing a curvilinear nose for locking bar 170. Moreover, O-ring 199 reduces noise that would otherwise result from contact between shoulders 202 and 190. Furthermore, it should now be appreciated that the locking mechanism floats in passageway 166 so that it is not subjected to excessive forces during use.

Figure 12A:
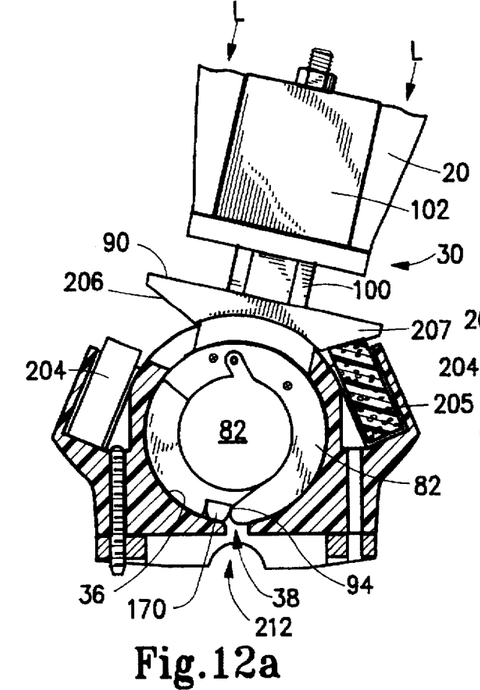
FIGS. 12(a), 12(b) and 12(c) respectively show the position of the ankle joint of the present invention in the plantarflexion, neutral and dorsiflexion positions.
Figure 12B:
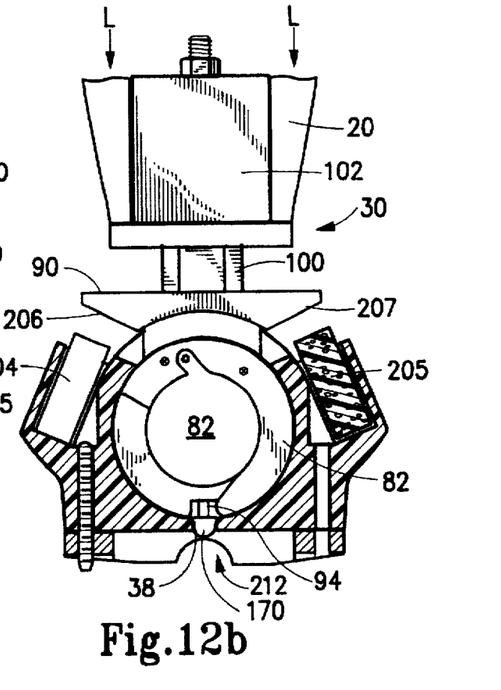
Figure 12C:
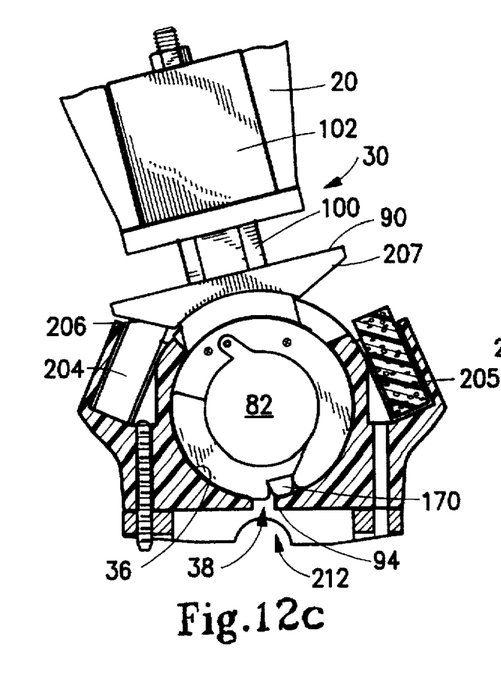

The operation of this locking mechanism may now be seen best with reference to FIGS. 12(a)-12(c) where it should be appreciated that the direction to the left of each of these figures is toward the toes 17 of foot portion 16. Accordingly, FIG. 12(a) relates to a plantarflexion position while FIG. 12(c) relates to a dorsiflexion position. Correspondingly, FIG. 12(b) relates to the "neutral" position. Turning to these figures, it may be seen that, in FIG. 12(a) a load "L" is placed on cap portion 102. However, since locking bar 170 is not aligned with channel 38, that is, locking bar 170 is in an abutting relation to arcuate sidewall 36, locking bar 170 is prevented from moving out of channel 94. Here, springs 178, 192 and 200 are compressed. This corresponds, of course, in the loading of a forward prosthetic foot during the person's gait. However, as a person shifts his/her weight onto the forward prosthetic foot so that the ankle joint 30 moves to the neutral position, shown in FIG. 12(b), spring 192 overcomes spring 180 and further compresses spring 180 which causes locking bar 170 to engage channel 38 so that relative rotation between head 82 and socket structure 32 is prevented. At this point, foot portion 16 may flex and, at the end of the stride, the amputee may get sufficient push-off as soon as the foot portion is locked in the neutral position.

With the prosthetic foot now in the rearward location of the stride, load "L" is removed so that locking bar 170 retracted into channel 94. At this time, when weight is taken off of the foot portion, torsional springs 74 act to return the ankle joint to the dorsiflexion position, shown in FIG. 12(c). This causes the toes 17 of foot portions 16 to move toward the shin portion 20 so that the foot may be brought forward for the next step. Spring 200 provides a push-off, and spring 180 acts to positively move rod 172 to disengage locking bar 170. To this end, it should be appreciated that springs 180 and 192 must be selected to have spring force constants that allow locking bar 170 to remain in the retracted position as the ankle joint moves from the position shown in FIG. 12(c) to the position shown in FIG. 12(a).

To further enhance use of the present invention, and to absorb the shocks incurred during walking, one or more cushions are provided for ankle joint 30. This is best shown in FIGS. 2, 7 and 12(a)-12(c), cushions 204 and 205 are respectively received in cushion cavities 47 and 49. Of these, cushion 205 is important in cushioning the effects of movement of ankle joint from the second (dorsiflexion) to the first (plantarflexion) position. When this happens, flat face 207 of plate 90 attacks cushion 205 whereby attenuating the motion of shank portion 80 with respect to socket structure 32 as it moves into the plantarflexion position. Likewise, flat face 206 of plate 90 will attack cushion 204 as shank portion 80 moves into the dorsiflexion position, as shown in FIG. 12(c).

Cushions 204 and 205 may be selected to have different shapes and degrees of compressibility, depending upon the activity in which the amputee engages. For example, for a running activity, the amputee may select relatively stiff cushions due to the greater impact forces encountered. However, for walking, softer cushions may be desired. For an activity such as horseback riding, it is desired to resist dorsiflexion of the foot so that the amputee may chose a stiffer, less compressible material for cushion 204. Indeed, the prosthetic device incorporating the pivotal ankle joint 30 of the present invention may be supplied with a set of varying cushions 204, 205 so that the amputee may customize the feel and use of the prosthetic device as desired. In the exemplary embodiment, cushions 204, 205 are hour-glass in shape.

Figure 13:
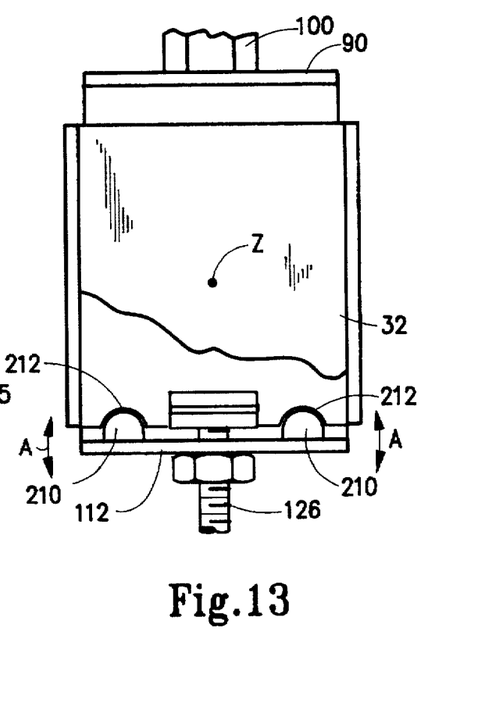
FIG. 13 is an end view in elevation showing the lateral bumper support structure according to the exemplary embodiment of the present invention.

Further, in order to more accurately imitate the action of a normal human ankle and to increase the balance of the amputee who uses the prosthetic device and the ankle joint of the present invention, lateral bumpers are provided to resiliently resist lateral flexion of the ankle joint. These bumpers are best shown in FIGS. 2, 8 and 13 where it should be appreciated that each bumper 210 is in the form of dome shaped post which are sized to be received in a recess 122 of base plate 12. When base plate assembly 110 is received in recess 22 of foot portion 16, bumpers 210 become trapped between base plate 112 and arcuate openings 212 in opposite lateral sides of plate 52. Thus, lateral pivotal motion about longitudinal axis "Z" in the direction of arrows "A" is permitted to some degree, but is limited by the resiliency of bumpers 210. Here again, the stiffness of compressibility and resiliency of bumpers 210 may be selected to the weight of the amputee and the intended use of the prosthetic device.

Figure 14A:
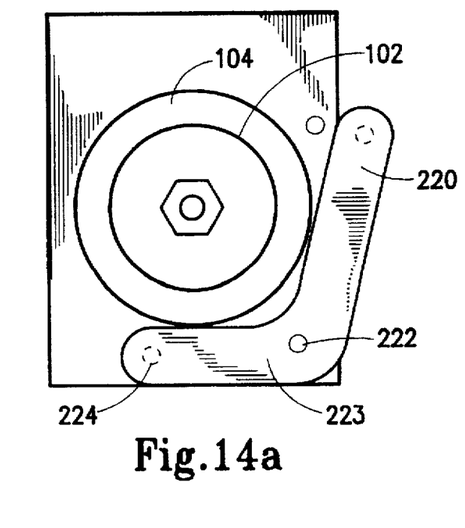
FIGS. 14(a) and 14(b) are top plan views showing the lock disable mechanism according to the exemplary embodiment of the present invention that operates to disable the locking mechanism.
Figure 14B:
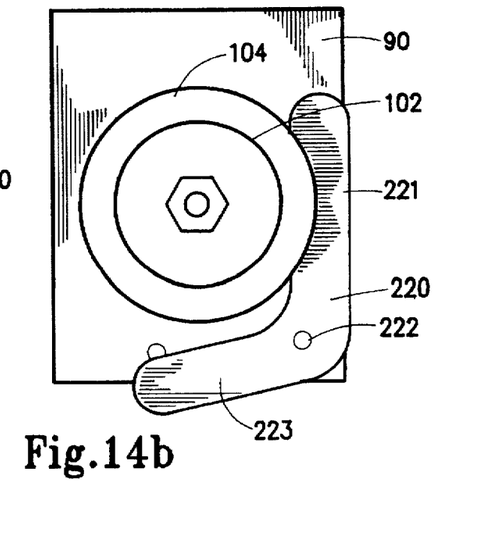
Figure 15:
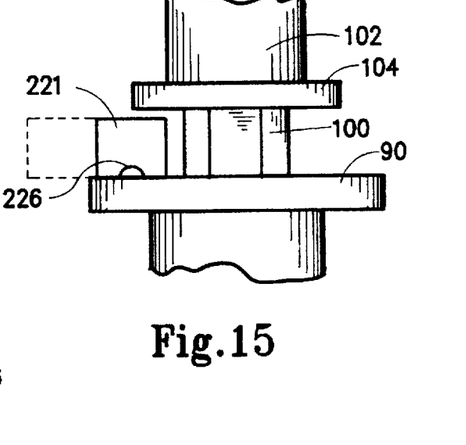
FIG. 15 is a side view in elevation showing the lock disable mechanism of FIGS. 14(a) and 14(b) in the lockout position.

Finally, as noted with respect to U.S. application Ser. No. 08/315,985, it is sometimes desirable to disable the locking mechanism described above. A primary example of such use would be the amputee desires to descend stairs. Should the locking mechanism be employed descent of a staircase, the locking of the joint into the neutral position would tend to cause the amputee to lunge forward opposite the prosthetic device is moved fully forward step. Therefore, a lock disable mechanism is provided as is best shown in FIGS. 14(a)-14(b) and 15. This optional lock disable mechanism is provided by an L-shaped arm 220 which is pivotally secured to plate 90 by means of a pivot post 222. In the position shown in FIG. 14(a), locking arm 220 is retained in a disengaged position so that it does not interfere with the movement of cap 102. This position is maintained by the ball and spring detent 224 shown in phantom. Should the amputee desire to disable the locking mechanism, however, locking arm 220 may be moved to a locking position as shown in FIG. 14(b). Here, lobe portion 221 is interposed between rim 104 of cap 102 to physically block movement of cap 102 toward plate 90, as is also shown in FIG. 15. Locking arm 220 is retained in the locking position in FIGS. 14(b) and FIG. 15 by means of releasable ball and spring detente 226 acting on lobe portion 223.

Based on the foregoing, it should be appreciate that the present ankle joint structure of the present invention provides many advantages over previous devices. However, it should be fully understood and appreciated that changes in the exact construction of ankle joint 30, especially as it relates to socket structure 32, the various cushions and bumpers described above, the locking mechanism disable, etc., could be made without departing from the inventive concepts of this invention. Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the scope intended for this invention.

I claim:

1. In a prosthetic leg device adapted to be worn by a human amputee wherein said leg device has a proximal end portion adapted to be secured to the amputee and a distal foot structure extending along a longitudinal axis, the improvement comprising an ankle joint disposed between said proximal end portion and said foot structure, said ankle joint including a matable socket and head assembly that has a socket disposed on one of said proximal end portion and said foot structure and a head sized to be matably received by said socket and disposed on another of said proximal end portion and said foot structure such that said head is relatively pivotable with respect to said socket about a pivot axis between first and second pivot positions corresponding to plantarflexion and dorsiflexion of said foot structure, respectively, and adjusting elements operative to permit selective adjustment in pitch of said socket and head assembly relative to said foot structure, said socket and head assembly including at least one lateral stabilizing element operative to resiliently resist lateral torque forces about the longitudinal axis, said ankle joint further including a load-sensitive locking mechanism associated with said socket and head assembly, said locking mechanism operative in response to a triggering compressive force between said socket and head in excess of a threshold magnitude to cause said head to lock with respect to said socket at a selected locking position between the first and second pivot positions thereby to prevent relative pivotal movement of said head and said socket and operative in an absence of the triggering compressive force to permit relative pivotal movement of said head and said socket between the first and second pivot positions.

2. The improvement according to claim 1 including a pair of lateral stabilizing elements operative to resist lateral torque forces in opposite rotational directions.

3. The improvement according to claim 2 including a mounting plate assembly including a mounting plate secured to said foot structure, said socket being secured to said mounting plate assembly and having a socket cavity, said head assembly including a head nestably received in the socket cavity and a shaft extending outwardly therefrom and secured to said proximal end portion of said leg device, said pair of lateral stabilizing elements being a pair of bumper elements interposed between said mounting plate and said socket, there being one of said bumper elements on each lateral side of said foot structure.

4. The improvement according to claim 1 including a spring element associated with said socket and head assembly and operative to bias said head into the second pivot position.

5. A prosthetic device adapted to be worn by a human amputee, comprising:

(a) a proximal portion adapted to be secured to a residual leg extremity of the amputee;

(b) a distal foot structure that extends along a longitudinal axis;

(c) a mounting base assembly adapted to be secured to said foot structure, said mounting base assembly including a mounting plate secured to said foot structure;

(d) a socket mounted to said mounting base assembly, said socket having a cavity formed therein;

(e) a shank portion including a head disposed in the cavity of said socket and a shaft adapted to mount to said proximal portion, said shank portion pivotable between first and second pivot positions on either side of a neutral position respectively corresponding to a plantarflexion, dorsiflexion and neutral positions of a human foot and ankle;

(f) a pair of bumper elements interposed between said mounting plate and said socket, there being one of said bumper elements on each lateral side of said foot structure; and (g) a load-sensitive locking mechanism associated with said socket and said head, said locking mechanism operative in response to a triggering compressive force between said socket and head in excess of a threshold magnitude to cause said head to lock with respect to said socket at a selected locking position between the first and second pivot positions thereby to prevent relative pivotal movement of said head and said socket and operative in an absence of the triggering compressive force to permit relative pivotal movement of said head and said socket between the first and second pivot positions.

6. A prosthetic device according to claim 5 including first and second cushion elements operative to attenuate relative pivotal movement of said shank portion at the first and second pivot positions, respectively.

7. A prosthetic device according to claim 6 wherein said socket has first and second cushion cavities formed therein and adapted to support said first cushion element and said second cushion element respectively, with said first cushion element located on one said of said socket rearwardly of said foot portion and said second cushion element located on another side of said socket forwardly of said first cushion element, and including a shoulder plate disposed on said shank portion and sized and oriented so as to attack said first and second cushions, respectively, as said shank portion pivots into said first and second positions.

8. A prosthetic device according to claim 5 including a swivel connector interconnecting said mounting plate and said socket.

9. A prosthetic device according to claim 8 including adjusting elements associated with said mounting plate and said socket and operative to permit selective adjustment in pitch therebetween.

10. A prosthetic device according to claim 9 wherein said adjusting elements include a pair of threaded bolts threadably received by said socket and having noses that bear against said mounting plate.

11. A prosthetic device according to claim 5 including a disable mechanism selectively operable to disable said load-sensitive locking mechanism such that said load-sensitive locking mechanism is prevented from locking said head and said socket at the selected locking position even in a presence of the triggering compressive force.

12. In a prosthetic leg device adapted to be worn by a human amputee wherein said leg device has a proximal end portion adapted to be secured to the amputee and a distal foot structure, the improvement comprising an ankle joint disposed between said proximal end portion and said foot structure, said ankle joint including a mounting plate assembly having a mounting plate secured to said foot structure and a socket secured to said mounting plate, said socket having a socket cavity, and including a head assembly including a head nestably received in the socket cavity, a shaft extending outwardly therefrom and secured to said proximal end portion of said leg device, and a shoulder plate disposed on said shaft for relative movement therewith, said socket, said head and said shaft defining a socket and head assembly with said head being relatively pivotable with respect to said socket about a pivot axis between first and second pivot positions corresponding to plantarflexion and dorsiflexion of said foot structure, respectively, and including a spring element associated with said socket and head assembly and operative to bias said head into the second pivot position, said socket and head assembly including a first cushion element independent of said spring element and operative to attenuate relative pivotal movement of said head at the first pivot position, said first cushion element being disposed on said socket and oriented so that said shoulder plate attacks said first cushion element when said head and said socket move into the first pivot position, and including a pair of bumper elements interposed between said mounting plate and said socket, there being one of said bumper elements on each lateral side of said foot structure.

13. The improvement according to claim 12 including a second cushion element operative to attenuate relative pivotal movement of said head at the second pivot position.

14. The improvement according to claim 12 wherein said ankle joint includes a load-sensitive locking mechanism associated with said socket and head assembly, said locking mechanism operative in response to a triggering compressive force between said socket and head in excess of a threshold magnitude to cause said head to lock with respect to said socket at a selected locking position between the first and second pivot positions thereby to prevent relative pivotal movement of said head and said socket and operative in an absence of the triggering compressive force to permit relative pivotal movement of said head and said socket between the first and second pivot positions.

15. The improvement according to claim 14 including a disable mechanism selectively operable to disable said load-sensitive locking mechanism such that said load-sensitive locking mechanism is prevented from locking said head and said socket at the selected locking position even in a presence of the triggering compressive force.

16. The improvement according to claim 12 including adjusting elements operative to permit selective adjustment in pitch of said socket and head assembly relative to said foot structure.

17. The improvement according to claim 12 including adjusting elements associated with said mounting plate and said socket and operative to permit selective adjustment in pitch therebetween.

18. The improvement according to claim 12 wherein said socket has a first cushion cavity adapted to removably support said first cushion element.

* * * * *